(12) United States Patent
Zhang et al.

(10) Patent No.: US 6,632,598 B1
(45) Date of Patent: Oct. 14, 2003

(54) DEPARAFFINIZATION COMPOSITIONS AND METHODS FOR THEIR USE

(75) Inventors: Guangrong Zhang, San Ramon, CA (US); Cheng-Zhi Yu, Pleasant Hill, CA (US); Sheng-Hui Su, San Ramon, CA (US); Krishan L. Kalra, Danville, CA (US); Ding Zhou, Pleasant Hill, CA (US)

(73) Assignee: BioGenex Laboratories, San Ramon, CA (US)

( * ) Notice: Subject to any disclaimer, the term of this patent is extended or adjusted under 35 U.S.C. 154(b) by 0 days.

(21) Appl. No.: 08/212,175

(22) Filed: Mar. 11, 1994

(51) Int. Cl.[7] .................................................. C12Q 1/00
(52) U.S. Cl. ........................... 435/4; 435/40.5; 435/267
(58) Field of Search ........................... 435/4, 267, 810, 435/960, 40.5; 424/3; 252/DIG. 8

(56) References Cited

U.S. PATENT DOCUMENTS

| | | | |
|---|---|---|---|
| 4,497,792 A | | 2/1985 | Gindler .......................... 424/3 |
| 4,530,781 A | * | 7/1985 | Gipp ........................... 252/546 |
| 4,911,915 A | * | 3/1990 | Fredenburgh .................... 424/3 |
| 5,032,503 A | | 7/1991 | Khanna et al. ................ 435/7.6 |
| 5,049,510 A | * | 9/1991 | Repasi ......................... 436/176 |
| 5,124,062 A | * | 6/1992 | Stevens ........................ 252/162 |
| 5,344,637 A | * | 9/1994 | Camiener ....................... 424/3 |

FOREIGN PATENT DOCUMENTS

| | | |
|---|---|---|
| AT | 394735 B1 | 11/1991 |
| DE | 3400195 A1 | 7/1986 |
| JP | 4-110400 | 4/1992 |

OTHER PUBLICATIONS

Abstract 62958g, "Cleaning solvent for removal of wax protective layer from new vehicles after storage and transportation" (1993) *Chemical Abstracts* vol. 118:187.

Jones, et al., "Comparision of Deparaffinization Agents for an Automated Immunostainer" (1993) *The Journal of Histotechnology* 16 (4):367–369.

Horobin, R.W., In "Histochemical and Immunochemical Techniques: Application to pharmacologhy and toxicology" (1991) Bach, P. and Baker, J., eds., Chapman & Hall, New York, NY pp. 1–9.

Ghassemifar, R. et al., "A double–embedding technique for thin tissue membranes" (1992) *Biotech. Histochem.* 67:363–366.

Mullin, L.S. et al., "Toxicology update isoparaffinic hydrocarbons: a summary of physical properties, toxicity studies and human exposure data" (1990) *J. Appl. Toxicol.* 10:135–142.

Abstract 133359e, "Degreasing detergents," Chemical Abstracts (1992) vol. 117:126.

Huang, S–N, et al. Application of Immunoflorescent Staining on Paraffin Sections Improved by Trypsin Digestion, Laboratory Investigation (1976) 35:383–390.

M.A. Hayat, ed., "Stains and Cytochemical Methods," (1993) Plenum Press, New York, NY.

Bannasch, et al. In "Histochemical and Immunochemical Techniques: Application to pharmacologhy and toxicology" (1991) Bach, P. and Baker, J., eds., *Chapman & Hall, New Yor, NY* pp. 187–223.

* cited by examiner

Primary Examiner—Ralph Gitomer
(74) Attorney, Agent, or Firm—James C. Weseman, Esq.; Law Offices of James C. Weseman

(57) ABSTRACT

Compositions and methods are provided for dewaxing wax-embedded biological specimens prior to histochemical analysis. The compositions and methods provided can effectively remove wax or improved wax-based embedding materials, particularly paraffin-based, from specimens during preparation for histochemical or other diagnostic analyses, while minimizing danger to users, achieving compatibility with automated use, and maintaining compatibility with downstream histochemical analyses, particularly immunostaining. Compositions of the invention comprise a paraffin-solubilizing organic solvent, a polar organic solvent, and a surfactant. Compositions can further comprise water. The method involves contacting a wax-embedded specimen with the dewaxing composition to solubilize the wax impregnating the specimen prior to histochemical analysis. The method can comprise the further step of washing the dewaxed specimen immediately after dewaxing with an aqueous wash composition comprising a detergent to remove residual dewaxing composition. Also provided is a kit for dewaxing a wax-embedded specimen, which comprises a dewaxing composition and can further comprise a second composition of (1) an immunostaining reagent or (2) an aqueous wash solution comprising a detergent for removing residual dewaxing solution.

18 Claims, No Drawings

DEPARAFFINIZATION COMPOSITIONS AND METHODS FOR THEIR USE

TECHNICAL FIELD

This application relates to compositions and methods for removal of wax from wax-embedded biological samples.

BACKGROUND

Paraffin has been used for many years as an embedding medium in the preparation of tissue specimens for sectioning in a microtome to produce specimen sections for histological studies. Such embedding processes generally include the well known steps of specimen fixation, dehydration, clearing, paraffin infiltration or impregnation, blocking or embedding in a block of paraffin, slicing the block and specimen into thin sections, mounting the sections on slides, removing the paraffin and solvents employed for this purpose (deparaffinizing), and staining the sections prior to microscopic analysis. The primary purpose of the embedding medium is to permit the specimens to be sectioned and mounted in the natural state. Plastic resins have also been used as embedding medium to provide a harder specimen that allows cutting of thinner sections. However, the use of paraffin-embedding has the advantage that the wax can be dissolved away from specimens prior to staining, allowing sections to be stained in the form of naked slabs of biopolymer and avoiding the extra difficulties and artifacts associated with the presence of unremovable resin-embedding medium (Horobin 1991).

Recent improvements in paraffin-embedding compositions broaden its applicability while maintaining its compatibility with downstream manipulation and analysis of samples. For example, an improved paraffin-based embedding material, which includes a mixture of paraffin and an effective amount of ethylene-vinyl acetate copolymer (0.5% to 5% by weight of paraffin) allows shorter infiltration time and thinner sections (U.S. Pat. No. 4,497,792). Another improvement, the double-embedding technique, yields sections of thin tissue membranes, such as rodent mesenteric membranes that usually measure only 10 microns in thickness. In this method several membranes are fixed and mounted on four needles located at the bottom of a plastic box and then embedded in agarose. The agarose block is removed, dehydrated in alcohol, cleared with HistoPetrol (tradename for a mixture of isoparaffin hydrocarbons), permeated with paraffin and sectioned. The observed tissue morphology is comparable to that obtained with methacrylate plastic embedding but is less time-consuming, less hazardous since no plastic hardener and activator are used, and makes immunohistochemical studies easier (Ghassemifar et al. 1992).

Consequently, deparaffinization of fixed, e.g. formalin fixed, paraffin embedded tissue sections is still a widely used methodology, particularly in hospital histopathology laboratories for immunodiagnostic purposes.

Xylene, which is a flammable, volatile and toxic organic solvent, is currently commonly used in protocols to solubilize paraffin for deparaffinization of specimen sections. Typically, the microscope slide-mounted specimen is immersed in a xylene bath until the paraffin is solubilized. The deparaffinized specimen is then washed with a series of alcohol solutions of decreasing alcohol concentration, typically as baths in which the specimen is immersed, to remove xylene before a final wash with water. Efforts have been made to replace xylene in the deparaffinization process with less toxic and less volatile solvents. Terpene oil (e.g. available under the tradename AmeriClear from Baxter Health Care Diagnostics, Inc. McGaw Park, Ill.) and isoparaffinic hydrocarbons (e.g. available under the tradename Micro-Clear from Micron Diagnostics, Inc., Fairfax, Va.) produced equal deparaffinization compared to xylene (Jones et al. 1993). However, a series of alcohol washes were still required to remove either solvent prior to the water wash to achieve compatibility with most types of staining, particularly immunohistochemical staining. Furthermore, the use of paraffin-embedded specimens with automated systems, such as immunostainers, is increasing.

Accordingly, there is still a need for deparaffinization compositions and methods that can effectively remove paraffin or improved paraffin-based embedding materials from specimens prior to histochemical or other diagnostic analyses, while minimizing danger to users, allowing compatibility with automated systems, and maintaining compatibility with downstream analyses. Deparaffinization compositions and methods that entail no or limited toxicity or carcinogenicity, produce no or minimal odors, reduce the quantity of toxic solvents used, minimize hazardous wastes, and/or decrease corrosiveness and flammability are needed.

Cited Literature

1. Horobin, R. W., In Histochemical and Immunochemical Techniques: Application to pharmacology and toxicology, (1991) Bach, P. and Baker, J., eds., Chapman & Hall, New York, N.Y. pp 1–9.
2. Ghassemifar, R. et al. (1992) "A double-embedding technique for thin tissue membranes" Biotech. Histochem. 67:363–366.
3. Jones, R. T. et al. (1993) "Comparison of deparaffinization agents for an automated immunostainer" J. Histotechnology 16:367–369.
4. Mullin, L. S. et al. (1990) "Toxicology update isoparaffinic hydrocarbons: a summary of physical properties, toxicity studies and human exposure data" J. Appl. Toxicol. 10:135–142.

SUMMARY OF THE INVENTION

Compositions and methods are provided for dewaxing wax-embedded biological specimens prior to histochemical or other analyses. The dewaxing compositions and methods provided can effectively remove wax or modified wax-based embedding materials, particularly paraffin or paraffin-based, from specimens prior to histochemical or other analyses, while minimizing danger to users, allowing compatibility with automated use, and maintaining compatibility with downstream analyses. Dewaxing compositions and methods that entail no or limited toxicity or carcinogenicity, produce no or minimal toxic odors, reduce the quantity of toxic solvents used, minimize hazardous wastes, and/or decrease corrosiveness and flammability are provided. The compositions and methods are especially useful for eliminating the use of xylene and for reducing the use of alcohol in preparation of tissue sections for immunohistochemical staining, particularly in hospital laboratories. Dewaxing compositions of the invention comprise a paraffin-solubilizing organic solvent, a polar organic solvent, and a surfactant as specified below in detail. Compositions can optionally comprise water.

A method for dewaxing biological specimens prior to histochemical or other analyses is provided. The method involves contacting a wax-embedded specimen with a dewaxing composition of the invention to solubilize the wax impregnating the specimen prior to histochemical analysis, such as immunohistochemical staining.

It is an object of the invention to eliminate the need for alcohol and alcohol baths for post-dewaxing washes by providing a method which involves contacting a dewaxed specimen, which has been dewaxed by a dewaxing composition of the invention, with an aqueous wash solution comprising a detergent to remove residual dewaxing composition.

A kit for dewaxing a wax-embedded specimen is provided. The kit comprises a dewaxing composition of the invention and can further comprise a second composition of (1) an immunostaining reagent or (2) an aqueous wash solution comprising a detergent for removing residual dewaxing solution.

The present invention eliminates or minimizes the use of toxic organic solvents in immunohistological laboratories. The compositions and methodology described herein effectively remove paraffin or other wax residue from tissue sections and have no adverse effect on the quality of tissue sections prepared for immunohistochemistry. Application of this dewaxing methodology can be extended to other applications where removal of wax from tissue sections are desired, such as in situ hybridization.

DESCRIPTION OF SPECIFIC EMBODIMENT

The present invention provides new dewaxing solvent compositions for removal of paraffin or other waxes from wax-embedded biological specimens for histochemical or other analyses. The compositions comprise a paraffin-solubilizing organic solvent, a polar organic solvent, and a surfactant. In further embodiments the compositions of the invention may be optionally diluted with water.

By "wax" is meant a composition used in the histochemical art for embedding biological specimens for histochemical or other analyses that is solid at room temperature, usually consists of a complex mixture of higher hydrocarbons often including esters of higher fatty acids and higher glycols, may be mineral, natural or synthetic in origin, is harder and more brittle than fats, is soluble in oils and fats, and can optionally contain additives that enhance its specimen-embedding properties. Paraffin is an example of a mineral wax most commonly used in the histochemical field. Paraffin is typically prepared by distillation of petroleum, and is a mixture of primarily solid saturated hydrocarbons.

By "histochemical" is meant to include the techniques and methods known as immunohistochemical, cytochemical, histopathlogic, enzyme histochemical, special stains, microtechnique, in situ hybridization, and the use of molecular probes. Texts illustrating histochemical techniques include "Histochemical and Immunochemical Techniques: Application to pharmacology and toxicology," (1991) Bach, P. and Baker, J., eds., Chapman & Hall, New York, N.Y. pp 1–9, and in "Stains and Cytochemical Methods," (1993) M. A. Hayat, ed., Plenum Press, New York, N.Y., which are incorporated herein by reference.

The paraffin-solubilizing organic solvent is a non-polar hydrocarbon or mixture of hydrocarbons (e.g. as from a petroleum distillate) that has a boiling point well above room temperature, preferably above 110° C., more preferably from about 140° C. to about 250° C., that is in liquid phase at the temperatures used with the present invention (usually 5° to 50° C.), and that is capable of dissolving paraffin used for embedding biological specimens. The paraffin-solubilizing solvent can be a complex mixture of long-chain linear and branched alkane hydrocarbons containing for example esters of fatty acids and higher glycols. The paraffin solubility of the solvent at 25° C. is typically at least 0.1 gram paraffin per 1 liter of solvent, preferably 0.1 gram per 100 ml of solvent, more preferably; 0.1 gram per 10 ml of solvent, and most preferably capable of a dissolving an amount of paraffin equal to about 50% of the solvent solutions weight. The paraffin-solubilizing solvent is further miscible with a polar organic solvent when used in a composition of the invention. Examples of paraffin-solubilizing organic solvents include aromatic hydrocarbons, aliphatic hydrocarbons, terpenes, other oils, and petroleum distillates. Preferred paraffin-solubilizing organic solvents have little or no toxic effects. Furthermore preferred solvents are those not classified by the Environmental Protection Agency as hazardous waste. A preferred paraffin-solubilizing solvent furthermore has a flash point higher than about 60° C. which minimizes flammability. A preferred solvent furthermore lacks toxicity, carcinogenicity, and corrosiveness. An isoparaffinic hydrocarbon is an example of a preferred paraffin-solubilizing solvent, in part because of its lack of toxicity, carcinogenicity, corrosiveness and flammability (Mullin et al. 1990). Preferred isoparaffins are branched aliphatic hydrocarbons with a carbon skeleton length ranging from approximately C10 to C15, or mixtures thereof. One preferred isoparaffin hydrocarbon mixture has a flashpoint of about 74° C. Another preferred paraffin-solubilizing solvent is a mixture of $C_{10}$ to $C_{50}$ branched or linear hydrocarbon chains having a distillation range from a boiling point of 150° C. to about 250° C., and has the general formula of $C_nH_{(2n\pm m)}$ where n=10–50 and m=0–4. Mineral spirits is another preferred paraffin-solubilizing organic solvent. A preferred terpene is limonene. Other terpenes that can be used include terpins, terpinenes and terpineols. Less preferably the solvent is an aromatic hydrocarbon solvent such as an alkylbenzene, e.g. xylene, or dialkylbenzene, e.g. toluene. Toluene and xylene are less preferred because of their toxicity and rating as hazardous waste. Furthermore, as discussed below, even when xylene or toluene are used in embodiments of the invention, subsequent alcohol washes are eliminated and replaced with a non-hazardous aqueous wash solution.

The paraffin-solublizing organic solvent in the composition is typically from about 25% to about 75% by volume of the dewaxing composition. Below the lower percent limit of paraffin-solubilizing organic solvent the dewaxing capability of the composition is significantly decreased. Above the upper limit of paraffin-solubilizing solvent an adverse affect on detergent solubility or water solubility occurs, which adversely affects the effectiveness of a subsequent aqueous wash. The upper limit of solvent can be selected among the upper limit values of 50%, 70%, and 75%, while the lower limit of solvent can be selected from the lower limit values of 25%, 35% and 40%, to obtain a variety of ranges for embodiments of the invention.

Because these compositions are typically prepared by combining components without a precise determination of the final volume of the composition or accounting for volume changes upon mixing, the percentages for each component are qualified with the term "about," with the understanding that one skilled in the art would appreciate the imprecision of the values as a consequence of composition preparation; however, preferably percentage values are taken to mean their precise value when volume changes upon mixing are accounted for.

The polar organic solvent serves the purpose of dissolving the paraffin-solubilizing solvent, surfactant and optionally water. The polar organic solvent is soluble in water to the extent of at least 1 g per 100 g water, preferably 5 g per 100 g water, more preferably 10 g per 100 g water and most preferably the polar organic solvent is miscible with water. Polar organic solvents include ketones and lower alcohols, which include polyhydroxy alcohols and glycols, and lower ethers. Preferred alcohols are $C_1$ to $C_5$ alcohols. Most preferred are ethanol, ethylene glycol, isopropanol, propylene glycol and mixtures thereof. A preferred ketone solvent is typically $C_3$ to $C_5$ ketone. Most preferred ketone solvents are acetone and methyl ethyl ketone. Preferred ethers are $C_2$ to $C_6$ ethers. Particularly preferred polar organic solvents are selected from the group consisting of methanol, ethanol, isopropanol, butanol, tert-butanol, allyl alcohol, acetone, ethylene glycol and propylene glycol, and a mixture thereof. Acetonitrile and dimethylformamide are less preferred polar organic solvents. Furthermore, the polar organic solvent can be a mixture of polar organic solvents.

The polar organic solvent in the composition is typically from about 25% to about 75% by volume of the composition. Preferably the amount is from about 35% to about 70%, more preferably from about 40% to about 65%, and most preferably from about 50% to about 60%. At what combination of components a composition is miscible or separates can readily be determined from a phase diagram showing phase separation for different relative amounts of the components of the solution/mixture.

Surfactants include cationic surfactants, anionic surfactants, non-ionic surfactants, and zwitterionic surfactants. A number of biological detergents (surfactants) are listed as such by Sigma Chemical Company on pages 1502–1508 of its 1991 Catalog of Biochemicals and Organic Compounds for Research and Diagnostic Agents. The surfactant serves the purpose of a detergent since it has both hydrophilic and hydrophobic properties. A surfactant for use in the invention is soluble in the solvent used in a composition of the invention. Preferred surfactants are detergents that are soluble in water, ethanol and acetone. Most preferred are those that do not substantially interfere with downstream histochemical analyses, which can be determined, for example, by immunostaining using a solution containing the surfactant.

Surfactants that can be used in compositions of the invention include cationic surfactants of the formula

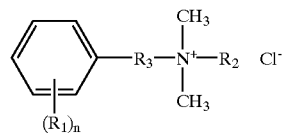

wherein $R_1$ is methyl, ethyl or propyl or isopropyl where n is 1 or 2; $R_2$ is an alkyl group selected from $C_8H_{17}$ to $C_{30}H_{61}$ or benzyl group; and $R_3$ is $(CH_2)_m$, where m is from 1 to 10, or $R_3$ is $(OCH_2CH_2)_p$ where p is from 1 to 10. Cationic surfactants of this formula are soluble in the polar organic solvents. Many preferred embodiments of the invention contain the cationic surfactant benzalkonium chloride or benzethonium chloride. Additional cationic detergents, not necessarily of this formula, include dodecyltrimethylammonium bromide, benzyldimethylhexadecyl ammonium chloride, cetylpyridinium chloride, methylbenzethonium chloride, and 4-picoline dodecyl sulfate.

Other surfactants that can be used in the compositions of the invention include anionic surfactants having the formula

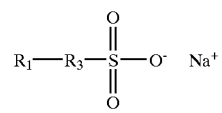

wherein $R_1$ is $C_6H_{13}$ to $C_{30}H_{61}$, and $R_3$ is $CH_2$ or phenyl group. Anionic surfactants of this formula are soluble in polar organic solvent. Examples of anionic detergents, not necessarily having this formula, include alginic acid, caprylic acid, cholic acid, 1-decanesulfonic acid, deoxycholic acid, 1-dodecanesulfonic acid, N-lauroylsarcosine, and taurocholic acid. Other anionic synthetic non-soap detergents, which are represented by the water-soluble salts of organic sulfuric acid reaction products, have in their molecular structure an alkyl radical containing from about 8 to 22 carbon atoms and a radical selected from the group consisting of sulfonic acid and sulfuric acid ester radicals. Examples of these are the sodium or potassium alkyl sulfates, derived from tallow or coconut oil; sodium or potassium alkyl benzene sulfonates; sodium alkyl glyceryl ether sulfonates; sodium coconut oil fatty acid monoglyceride sulfonates and sulfates; sodium or potassium sales of sulfuric acid esters of the reaction product of one mole of a higher fatty alcohol and about 1 to 6 moles of ethylene oxide per molecule and in which the alkyl radicals contain from 8 to 12 carbon atoms; the reaction product of fatty acids esterified with isethionic acid and neutralized with sodium hydroxide, sodium or potassium salts of fatty acid amide of a methyl tauride; and sodium and potassium salts of $SO_3$-sulfonated $C_{10}$–$C_{24}$ α-olefins.

Further surfactants that can be used in compositions of the invention include non-ionic surfactants having the formula

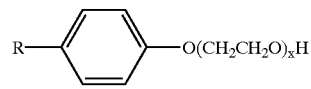

wherein R is a linear or branched C1 to C10 alkyl group and X is an integer from 5 to 40. Most preferably R is

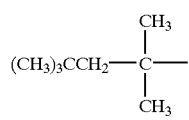

Non-ionic surfactants of this formula are soluble in polar organic solvents. Examples of nonionic detergents, not necessarily having this formula, include decanoyl-N-methylglucamide, diethylene glycol monopentyl ether, n-dodecyl β-D-glucopyranoside, polyoxyethylene ethers of fatty acids (particularly $C_{12}$–$C_{20}$ fatty acids, (e.g., sold under the trade name Triton), ethylene oxide condensates of fatty alcohols e.g. sold under the name Lubrol), polyoxyethylene sorbitan fatty acid ethers (e.g., sold under the trade name Tween), and sorbitan fatty acid ethers (e.g., sold under the trade name Span). Nonionic synthetic detergents made by the condensation of alkylene oxide groups with an organic hydrophobic compound. Typical hydrophobic groups include condensation products of propylene oxide with propylene glycol, alkyl phenols, condensation product of propylene oxide and ethylene diamine, aliphatic alcohols having 8 to 22 carbon atoms, and amides of fatty acids. Also nonionic detergents such as amine oxides, phosphine oxides and sulfoxides having semipolar characteristics and be removed. Specific examples of long chain tertiary amine oxides include dimethyldodecylamine oxide and bis-(2-hydroxyethyl)dodecylamine. Specific examples of phosphine oxides are found in U.S. Pat. No. 3,304,263 which issued Feb. 14, 1967, and include dimethyldodecylphosphine oxide and dimethyl-(2-hydroxydodecyl)phosphine oxide. A preferred non-ionic detergent surfactant is Triton X-100, which is a tradename for a polyoxyethylene ether of fatty acids particularly $C_{12}$–$C_{20}$ fatty acids).

Zwitterionic surfactants include known compounds of the formula N-alkyl-N,N,-dimethyl-3-ammonia-1-propanesulfonate. Examples of zwitterionic detergents include 3-[(3-cholamidopropyl)-dimethylammonio]-1-propanesulfonate (commonly abbreviated CHAPS), 3-[(cholamidopropyl) dimethylammonio]-2-hydroxy-1-propanesulfonate (generally abbreviated CHAPSO), N-dodecyl-N-methyl-3-ammonio-1-propanesulfonate, and lyso-α-phosphatidyl-choline.

The surfactant in the composition is typically from about 0.5% to about 20% weight to volume (g/100 ml) of the composition. Below the lower limit of surfactant poor solubility of wax in the composition is observed. The upper limit of surfactant is a factor of the surfactant's solubility limit. The amount of surfactant is preferably from 0.5% to about 15% by weight, more preferably from about 0.5% to about 10% surfactant by weight, most preferably from about 0.5% to about 5% by weight.

Compositions of the invention can also contain water. Most preferably the water in a composition is a saturating amount of water. Above this upper limit phase separation of the composition occurs. Typically water is less than or about 10% by volume of the composition. Some embodiments of the invention, for example as exemplified in the Examples, have less than about 7% water, some have from about 0.5% to about 1.5% water, and still others have less than about 1% water by volume.

In some embodiments of the invention, the dewaxing compositions or the aqueous wash solutions contain buffer, salts or other reagents useful for wax-solubilization, washes, or subsequent histochemical steps, so long as such optional reagents do not interfere with the wax-solubilizing capability of the composition, the efficiency of a washing step, or subsequent histochemical steps. Reagents useful for subsequent processing or histochemical steps include carboxylic acid esters, enzymes such as lipases, and nucleophilic reagents as described in co-owned U.S. application Ser. No. 07/821,931, filed Jan. 16, 1992 (Published as PCT/US93/07550), entitled "Enhancement of immunochemical staining in aldehyde-fixed tissues," which is incorporated herein by reference. Optional agents can serve to expose or enhance aldehyde-fixed tissue antigen(s) for inmunohistochemical staining. Additional optional reagents include anti-microbial agents and stabilizers that increase composition shelf life. Such anti-microbial agents and stabilizers are well known in the field. Such reagents are typically used at extremely small percentages, typically below 0.1%, compared to the main components. Preferred reagents are those that do not interfere with downstream histochemical analyses.

Each of the individual components of the compositions of the invention is either commercially obtainable, is isolated from natural sources using known procedures, or is synthesized according to known procedures.

Compositions of the invention are prepared by simple mixing of the components in the indicated amounts.

Methods of preparing biological samples for sectioning via wax- or paraffin-impregnation are generally well known and easily carried out. The process is quite simple and involves contacting a wax-embedded specimen with a dewaxing composition of the invention to solubilize the wax that impregnates the specimen prior to hiochemical analyses, such as immunostaining. The method optionally comprises a further step of contacting the dewaxed specimen immediately after dewaxing with an aqueous washing composition comprising a detergent to remove residual dewaxing composition.

Although the dewaxing process is typically and conveniently carried out at room temperature, without the need for a temperature controlled bath, a more precise control of the required time for satisfactory dewaxing and washing is available if temperature-controlled baths are used. Heating decreases processing time. Operable temperatures range from 5° to 50°, preferably from about 15° C. to about 45° C., and more preferably from about 25° C. to about 40° C.

Typically the wax-embedded specimen is contacted with a composition of the invention for a time sufficient to solubilize all or part of the wax embedding the specimen. Factors influencing the solubilization time include temperature, thickness of the specimen section, and wax composition. Time for any particular specimen type is best determined empirically. However, five minutes of contact is usually sufficient for specimens mounted on microscope slides. A sectioned specimen, typically affixed to a microscope slide, is contacted with a composition of the invention in any number of ways. Preferably, the specimen is immersed in a bath containing the composition, or alternatively an amount of composition sufficient to solubilize the wax can be placed on the specimen such that the specimen is covered by the composition. After sufficient time of contact has elapsed for wax solubilization to occur, the specimen is removed from contact with the composition, and excess composition is removed from the specimen, for example by draining or blotting. Optionally, a second or even a further deparaffinization step or steps are performed, preferably with fresh dewaxing composition, to further assure removal of wax from the specimen.

The invention decreases or eliminates the requirement of alcohol baths for post-dewaxing washes. Post dewaxing washes are not always required with compositions of the invention. If such a step proves desirable (because of a particularly sensitive immunostaining procedure, for example) the dewaxed specimen can be contacted with an aqueous wash composition of the invention which comprises a detergent. A preferred wash solution comprises a buffer and a detergent. Preferably the detergent is non-ionic. A preferred buffer/detergent wash solution is phosphate buffered saline with about 1% nonionic surfactant polyoxyethylene ether such as BRIJ-35 (tradename for the nonionic surfactant polyoxyethyleneglycol dodecyl ether or polyoxyethylene (23) lauryl ether). Typically the amount of detergent is from about 0.1% to about 5% (weight to volume), preferably from about 0.1% to 2%, and most preferably about 1%. The pH of the wash composition is most preferably neutral to avoid adversely affecting downstream histochemical, particularly immunochemical, analyses. The pH can range from about 4 to about 10, preferably from about 5 to about 8, more preferably from about 7.2 to about 7.6, and most preferably 7.4 to about 7.5. A preferred buffer is one which does not interfere with downstream analyses and/or can be readily removed with a subsequent aqueous wash or optional water wash. Phosphate buffered saline or Tris containing buffers are examples of preferred buffers. Washing can occur in any number of ways, including immersion in a wash bath, flowing wash solution over the specimen, or diffusing or permeating the wash solution throughout the specimen. Wash time is best determined empirically; however, five minutes is usually sufficient. Multiple rinses and larger amounts of washing solution can be used to achieve increased removal of deparaffinization solution. A single wash is sufficient for most purposes; however, a second wash is preferred if removal is not sufficient. Optionally, the specimen is finally washed or rinsed in water. A water wash of 3 minutes is usually sufficient for the most rigorous conditions. After washing the specimen is then ready for histochemical or other analyses.

The compositions of the invention, including the wash solutions, are compatible with automated staining systems, as described, for example, in co-owned application U.S. Ser. No. 08/129,243, which is hereby incorporated by reference. Dewaxed slides can be provided to an automated stainer or an automated stainer can be provided with compositions of the invention to allow automated dewaxing of the slides prior to automated analyses.

Although preferred surfactants and other components used in a dewaxing solution of the invention are those that do not typically interfere with downstream analyses, particularly at the residual levels remaining on the specimen after the wash procedures, methods known in the art may be applied to enhance surfactant (or other component) removal should residual surfactant (or other component) cause problems in downstream analyses. For residual surfactant removal soluble compounds known to bind a surfactant may be included in an aqueous wash solution. For example, cyclodextrins are known to bind certain surfactants (U.S. Pat. No. 5,032,503) and may be included in a wash solution. Protein, such as bovine serum albumin, can be included in a wash solution to bind and remove residual surfactant. In one preferred embodiment, a surfactant that does not interfere with the downstream analyses, but that can displace the residual surfactant, can be used in an aqueous wash solution. This displacing surfactant is preferably easily removed with a water wash. Polyoxyethylene alkyl ether type non-ionic surfactants are a preferred wash surfactant. BRIJ-35 (tradename for polyoxyethyleneglycol dodecyl ether) is an example of one such surfactant.

Also provided is a kit for dewaxing a wax-embedded specimen. The kit comprises a container of dewaxing composition and can further comprise a second container of (1) an histochemical staining reagent or (2) an aqueous wash solution of the invention comprising a detergent for removing residual dewaxing solution. The containers are typically located in a receptacle specifically adapted to hold them. Preferably the wash solution contains a buffer and a detergent. In one embodiment the histochemical staining reagent is an immunostaining reagent. In another embodiment the histochemical staining reagent is an in situ hybridization reagent. The kit can be a component of a larger kit for histochemical analyses, such as in a kit for use with automated immunostainers. Any of the other reagents described herein can be used in the kit in combination with the specified components.

The compositions and methods of the invention are suitable for use in a variety of histochemical applications, particularly immunochemical staining. In situ hybridization with nucleic acid probes is another particularly pertinent use compatible with compositions and methods of the invention.

The present invention eliminates or minimizes the use of certain toxic organic solvents in immunohistological laboratories. The compositions and methodology described herein effectively removes paraffin and other waxes residues from tissue sections and has no adverse effect on quality of tissue sections prepared for immunohistochemistry. Application of this deparaffinization methodology can be extended to other applications where removal of paraffin and other waxes from tissue sections are necessary. In preferred embodiments using isoparaffins, the compositions have a very low order of acute toxicity, being practically non-toxic by oral, dermal and inhalation routes. In addition the compositions allow a method of deparaffinization that eliminates the use of graded alcohol washes. Accordingly, the embodiments of the present invention meet the need of providing compositions and methods that minimize dangers to the user and minimize the creation of hazardous waste.

The invention now being generally described, the same will be better understood by reference to the following detailed examples which are provided for illustration and are not to be considered as limiting the invention unless so specified.

EXAMPLES

Example 1

Deparaffinizing Compositions

The following examples of deparaffinization compositions are presented by way of illustration of embodiments of the invention and not intended to limit the invention.

Composition 1 was prepared by mixing reagent alcohol (275 ml; a premixed solution of 90% v/v anhydrous ethyl alcohol, 5% v/v methyl alcohol and 5% v/v isopropyl alcohol), limonene (100 ml), water (25 ml) and benzalkonium (20 g).

Composition 2 was prepared by mixing reagent alcohol (100 ml), limonene (100 ml) and benzalkonium (15 g).

Composition 3 was prepared by mixing reagent alcohol (100 ml), isoparaffinic hydrocarbon (100 ml) and benzalkonium (15 g). The isoparaffinic hydrocarbon solvent used in the compositions of this example is available as MicroClear, a tradename of Micron Diagnostics, Inc., for their isoparaffinic hydrocarbon solvent.

Composition 4 was prepared by mixing reagent alcohol (50 ml), limonene (50 ml), water (0.6 ml) and benzalkonium (10 g).

Composition 5 was prepared by mixing reagent alcohol (50 ml), isoparaffin (50 ml), water (0.6 ml) and benzalkonium (15 g).

Composition 6 was prepared by mixing reagent alcohol (100 ml), isoparaffin (50 ml), mineral spirits (50 ml) and benzalkonium (15 g).

Composition 7 was prepared by mixing reagent alcohol (50 ml), isoparaffin (50 ml), water (0.9 ml) and Triton-X100 (10 g).

Composition 8 was prepared by mixing reagent alcohol (65 ml), isoparaffin (45 ml) water (0.5 ml) and BRIJ-35 (1.0 g).

Composition 9 was prepared by mixing reagent alcohol (54 ml), isoparaffin (35 ml) water (1.0 ml) and BRIJ-35 (2.5 g).

Example 2

Deparaffinization

Deparaffinization of slide mounted tissue specimens using Compositions 1–9 of Example 1 was performed prior to immunohistological analyses. Human tissues used in this study included skin, pancreas, tonsil, spleen, lung, breast, prostate, colon carcinoma, melanoma and astrcytoma. Compositions 1–9 were tested individually. Each 4 micron paraffin embedded tissue section on a slide was covered with 1.9 ml of a deparaffinization Composition 1–9. After 5 minutes, the deparaffinization composition was removed and 1.0 ml of fresh deparaffinization composition was added to cover the section for an additional 5 minutes. A third deparaffinization of the section for an additional 5 minute in fresh deparaffmiiiation composition was also carried out. Immediately after the final deparaffinization, slides were rinsed in an aqueous wash composition of PBS with 1% BRIJ-35 for 5 minutes. The slides were then rinsed in tap water for 3 minutes and used for immunohistochemistry.

Example 3

Deparaffinization

In this Example a second method for deparaffinization of slide mounted tissue specimens using Compositions 1–9 of Example 1 was performed prior to immunohistological analyses. Human tissues used in this study included skin, pancreas, tonsil, spleen, lung, breast, prostate, colon carcinoma, melanoma and astrocytoma. Compositions 1–9 were tested individually. Each slide containing paraffin embedded tissue sections was immersed in a glass-jar containing 60 ml of one of the deparaffinization Compositions 1–9. After 5 minutes, the deparaffinization composition was decanted and replaced with fresh deparaffinization composition and the slides were deparaffinized for an additional 5 minutes. A third five-minute deparaffinization was also carried out. Immediately after deparaffinization, slides were rinsed in an aqueous wash composition containing PBS with 1% BRIJ-35 for 5 minutes, rinsed in tap water for 3 minutes, and used for immunohistochemistry.

Example 4

Deparaffinization in Xylene

A widely used, standard deparaffinization protocol involving xylene was performed as a control. Slides containing paraffin embedded tissue sections were immersed in 100% xylene for 5 minutes followed by two changes in fresh 100% xylene for 5 minutes each. Afterwards, the slides were immersed in a bath of 100% alcohol twice for three minutes each time. The slides were then immersed sequentially in baths of 95% alcohol, 85% alcohol and then 75% alcohol for three minutes in each bath. The slides were fully rinsed in tap water for 3 minutes and used for immunohistochemistry. A series of slides were prepared following this protocol but substituting either limonene or MicroClear for xylene.

Example 5

Effectiveness of Paraffin Removal

The deparaffied slides prepared as in Examples 2, 3, and 4 were examined for effectiveness of paraffin removal. After the slides were deparaffinized with deparaffinization Compositions 1–9 and washed aqueous wash composition of PBS with 1% BRIJ-35, no paraffin residue was left on the sections or other location of the slides. No paraffin residue was detected on sections or slides deparaffinized with the control procedure using xylene and hydrated with graded alcohols and water. There was no discernible difference in effectiveness for paraffin removal among xylene, limonene, isoparaffin, and deparaffinization Compositions 1–9 of Example 1.

Example 6

Effect of Deparaffinization Solvents on Immunohistochemistry Staining

Normal or tumorous human tissues including skin, pancreas, tonsil, spleen, lung, breast, prostate, colon carcinoma, melanoma and astrocytoma, were stained with corresponding monoclonal antibodies to determine effects of deparaffinization compositions on immunohistochemical staining. Xylene deparaffinized tissue section slides were used as standard controls. Slides containing sections deparaffinized as described in Examples 2, 3 and 4 were examined for compatibility to immunohistological analyses. Deparaffinized slides were immersed in Block Solution I (a tradename of BioGenex, San Ramon, Calif., for a solution of PBS and 3% hydrogen peroxide), for 10 minutes. Each slide was then rinsed in PBS twice, 5 minutes each time. Two hundred microliters of primary antibodies (obtained from BioGenex under the tradename Ready to Use Antibodies) were incubated with their respective sections for 30 minutes or 2 hours according to individual staining protocols provided by the supplier. The following monoclonal antibodies were used in immunohistochemistry: anti-human cytokeratin cocktail, anti-NSE, anti-insulin, anti-LCA, anti-kappa chain, anti-Q-band, anti-L26, anti-factor VIMI, anti-CEA, anti-p53, anti-Cerb-2, anti-PR, anti-vimentin, anti-PSA, anti-H45, anti-S-100 and anti-GFAP. The slides were then washed in PBS three time, 5 minutes each. After a 20 minute incubation with biotinylated secondary antibodies (available under the tradname Super Sensitive Link from BioGenex), the slides were washed in PBS three times, 5 minutes each time. Slides were then incubated with a stock solution of peroxidase-conjugated streptavidin (available under the tradename Super Sensitive Label from BioGenex) for 20 minutes and washed three times in PBS. The chromogenic reaction was carried out using AEC (3-amino-9-ethylcarbozole) for peroxidase and Fast Red for alkaline phosphatase. After color development, each slide was rinsed in tap water, counterstained, mounted and examined by light microscopy.

Intensity of immunostaining reactivity was evaluated by a light-microscope. There was no difference in immunostaining intensity among slides deparaffinized with deparaffinization Compositions 1–9 and the control deparaffinized with xylene.

Example 7

Effect of Frequency of Solvent Composition Changes on Deparaffinization

Composition 8 was used to evaluate the effect of frequency of composition changes on deparaffinization. The extent of paraffin removal was determined by visual inspection of the treated slides. In the presence of residual paraffin water formed numerous, small droplets on the slide's surface, which had a waxy-appearance. Upon complete deparaffinization water formed an even film on the slide surface. After slides were immersed in Composition 8 for five minutes and then washed with aqueous wash buffer: PBS containing 1% BRIJ-35, there was residual paraffin left on the slides. There was no discernable residual paraffin left on the slides when specimens were deparaffied by immersion in Composition 8 for five minutes, followed by immersion in a fresh solution of Composition 8 for five minutes, and finally washed with the aqueous wash solution. Specimens were also deparaffinized by a protocol of two changes of Composition 8 followed by the aqueous wash. There was no difference in terms of intensity of immunohistochemical staining among the three deparaffinization conditions.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A process for removing wax from a wax-embedded biological tissue specimen, said process comprising contacting said wax-embedded tissue specimen with a dewaxing composition comprising a paraffin-solubilizing organic solvent selected from the group consisting of aromatic hydrocarbons, terpenes and isoparaffinic hydrocarbons, a polar organic solvent, and a surfactant to solubilize the wax associated with the specimen.

2. A process as recited in claim 1, which further comprises the step of washing said tissue specimen after said contacting step with an aqueous wash solution comprising a detergent to remove residual dewaxing composition from said tissue specimen.

3. A process as recited in claim 1 wherein the dewaxing composition comprises:
   (a) at least one paraffin-solubilizing organic solvent selected from the group consisting of aromatic hydrocarbons, terpenes and isoparaffinic hydrocarbons, said paraffin-solubilizing organic solvent comprising from about 25% to about 75% by volume of said composition;
   (b) at least one water soluble polar organic solvent, said water soluble polar organic solvent comprising from about 25% to about 75% by volume of said composition;
   (c) at least one water soluble surfactant, said water soluble surfactant comprising from about 0.5% to about 20% by weight to volume of said composition.

4. A process as recited in claim 1, which further comprises water at less than or about 10% by volume.

5. A process as recited in claim 1, wherein the paraffin-solubilizing organic solvent is limonene.

6. A process as recited in claim 1, wherein the paraffin-solubilizing organic solvent comprises an isoparaffinic hydrocarbon.

7. A process as recited in claim 1, wherein the paraffin-solubilizing organic solvent is an alkylbenzene or dialkylbenzene.

8. A process as recited in claim 1, wherein the polar organic solvent is selected from the group consisting of C-1 to C-5 alcohols, C-3 to C-5 ketones, and C-2 to C-6 ethers.

9. A process as recited in claim 8, wherein the polar organic solvent comprises a solvent or a mixture of solvents selected from the group consisting of methanol, ethanol, isopropanol, butanol, acetone, ethylene glycol, and propylene glycol.

10. A process as recited in claim 8, wherein the polar organic solvent is methanol, ethanol, propanol, isopropanol, tert-butanol or allyl alcohol.

11. A process as recited in claim 1, wherein the surfactant is present at about 0.5% to about 15% weight to volume.

12. A process as recited in claim 1, wherein the surfactant comprises a cationic or anionic surfactant.

13. A process as recited in claim 12, wherein the surfactant is a cationic surfactant having the formula

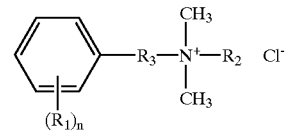

wherein $R_1$ is methyl, ethyl or propyl or isopropyl where n is 1 or 2; $R_2$ is an alkyl from $C_8H_{17}$ to $C_{30}H_{61}$ or a benzyl group; and $R_3$ is $(CH_2)_m$ where m is from 1 to 10, or $R_3$ is $(OCH_2CH_2)_p$ where p is from 1 to 10.

14. A process as recited in claim 13, wherein the cationic surfactant is benzalkonium chloride or benzethonium chloride.

15. A process as recited in claim 12, wherein the surfactant is an anionic surfactant having the formula

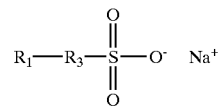

wherein $R_1$ is $C_6H_{13}$ to $C_{30}H_{61}$ and $R_3$ is $CH_2$ or a phenyl group.

16. A process as recited in claim 1, wherein the surfactant is a non-ionic surfactant.

17. A process as recited in claim 16, wherein the non-ionic surfactant has the formula

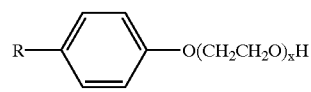

wherein R is a linear or branched C1 to C10 alkyl group and X is from 5 to 40.

18. A process as recited in claim 17, wherein the non-ionic surfactant contains polyoxyethylene ethers of $C_{12}$ to $C_{20}$ fatty acids.

* * * * *